United States Patent [19]
Macor

[11] Patent Number: 5,849,739
[45] Date of Patent: Dec. 15, 1998

[54] 5-ARYLINDOLE DERIVATIVES

[75] Inventor: John Eugene Macor, Penfield, N.Y.

[73] Assignee: Pfizer Inc., New York, N.Y.

[21] Appl. No.: 600,931

[22] PCT Filed: Jul. 4, 1994

[86] PCT No.: PCT/IB94/00195

§ 371 Date: Feb. 29, 1996

§ 102(e) Date: Feb. 29, 1996

[87] PCT Pub. No.: WO95/06636

PCT Pub. Date: Mar. 9, 1995

Related U.S. Application Data

[63] Continuation-in-part of Ser. No. 115,282, Aug. 31, 1992, abandoned.

[51] Int. Cl.[6] ............ C96D 209/04; C96D 401/04; C96D 403/04; A61K 31/40
[52] U.S. Cl. .......... 514/247; 514/255; 514/256; 544/238; 544/333; 544/405
[58] Field of Search .............. 544/224, 238, 544/333, 405; 514/247, 254

[56] References Cited

U.S. PATENT DOCUMENTS

| | | | |
|---|---|---|---|
| 2,773,875 | 12/1956 | Finkelstein | 548/466 |
| 3,037,031 | 5/1962 | Lewis et al. | 548/466 |
| 4,252,803 | 2/1981 | Webb | 424/248.5 |
| 4,803,218 | 2/1989 | Stanley et al. | 548/466 |
| 4,855,314 | 8/1989 | Oxford et al. | 514/415 |
| 5,208,248 | 5/1993 | Baker et al. | 514/384 |
| 5,348,968 | 9/1994 | Lavielle | 548/468 X |
| 5,409,941 | 4/1995 | Nowakowski | 514/33 |
| 5,451,588 | 9/1995 | Baker et al. | 514/323 |

FOREIGN PATENT DOCUMENTS

| | | |
|---|---|---|
| 465398 | 1/1992 | European Pat. Off. . |
| 497512 | 8/1992 | European Pat. Off. . |
| 74527 | 4/1954 | Netherlands . |
| 74786 | 5/1954 | Netherlands . |
| 851780 | 10/1960 | United Kingdom . |
| 886684 | 1/1962 | United Kingdom . |
| 893707 | 4/1962 | United Kingdom . |
| 966562 | 8/1964 | United Kingdom . |
| 2081717 | 2/1982 | United Kingdom . |
| 9206973 | 4/1992 | WIPO . |
| 9311106 | 6/1993 | WIPO . |
| 9314087 | 7/1993 | WIPO . |
| 9318032 | 9/1993 | WIPO . |
| 9320073 | 10/1993 | WIPO . |
| 9321177 | 10/1993 | WIPO . |

(List continued on next page.)

OTHER PUBLICATIONS

Bader, et al., *J. Am. Chem. Soc.*, 79, 5686–5689 (1957).
Gray, *J. Org. Chem.*, 23, 1453–1454 (1958).
Moore, et al., *J. Org. Chem.*, 29, 2860–2864 (1964).
Cain, et al., *J. Am. Chem. Soc.*, 105 908, 911, 912 (1983).
Markowitz, et al. *J. Neurosci.*, 7 (12) 4736 (1987).
Lee, et al., *Brain Res.*, 303–305 (1993).
P.P.A. Humphrey, et al., *Br. J. Pharmacol.*, 94, 1128 (1988).
W. Fernik, et al., *Br. J. Pharmacol.*, 96, 83 (1989).
Reggent for Org. Syn, 1, 112 (1967).
Mohr, et al., *Tetrahedron*, 38(1), 147–152 (1982).
Friderichs, et al., *Chem. Ab.*, 83, 28056 (1975).
Kiyooka, et al., *J. Org. Chem.*, 5409 (1989).
Hamada, et al., *Chem. Pharm. Bull.*, 1921 (1982).
Lee, et al., *Soc. Neurosci* No. 1993 Meeting 19 (Part 2), #565.6.
Moskowitz, *7th World Congress on Pain* Aug. 1993, #667.
Leonard, et al., *Neuropharm.*, 11, 373–384 (1972).

*Primary Examiner*—Mukund J. Shah
*Assistant Examiner*—Deerak R. Rao
*Attorney, Agent, or Firm*—Peter C. Richardson; Paul H. Ginsburg; Grover F. Fuller, Jr.

[57] ABSTRACT

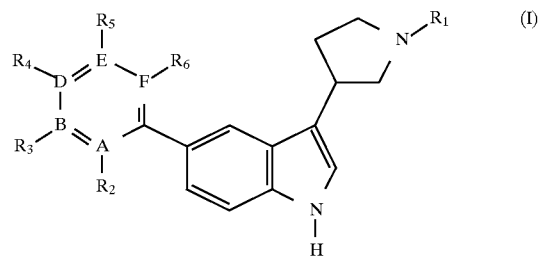

Compounds of formula (I), wherein A, B, D, E, and F are each independently nitrogen or carbon; $R_1$ is hydrogen, $C_1$ to $C_6$ alky, $-(CH_2)_n R_7$, or $C_1$ to $C_3$ alkyl-aryl; $R_2$, $R_3$, $R_4$, $R_5$ and $R_6$ are each independently hydrogen, $C_1$ to $C_6$ alkyl, aryl, $C_1$ to $C_3$ alkyl-aryl, halogen, cyano, nitro, $-(CH_2)_m NR_8 R_9$, $-(CH_2)_m OR_9$, $-SR_9$, $-SO_2 NR_8 R_9$, $-(CH_2)_m NR_8 SO_2 R_9$, $-(CH_2)_m NR_8 CO_2 R_9$, $-(CH_{2m} NR_8 COR_9$, $-(CH_2)_m CONR_7 R_9$, or $-(CH_2)_m CO_2 R_9$; $R_2$ and $R_3$, $R_3$ and $R_4$, $R_4$ and $R_5$, and $R_5$ and $R_6$ may be taken together to form a 5- to 7-membered alkyl ring, a 6-membered aryl ring, a 5- to 7-membered heteroalkyl ring, having 1 heteroatom of N, O, or S, or a 5- to 6-membered heteroaryl ring having 1 or 2 heteroatoms of N, O, or S; $R_7$ is $-OR_{10}$, $-SR_{10}$, $-SO_2 NR_{10} R_{11}$, $-NR_{10} SO_2 R_{11}$, $-NR_{10} CO_2 R_{11}$, $-NR_{10} COR_{11}$, $-CONR_{10} R_{11}$, or $-CO_2 R_{10}$; $R_8$, $R_9$, $R_{10}$ and $R_{11}$ are each independently hydrogen, $C_1$ to $C_6$ alkyl, or $C_1$ to $C_3$ alkyl-aryl; m is 0, 1, or 2; n is 2, 3, or 4; and the above aryl groups and the aryl moieties of the above alkyl-aryl groups are each independently phenyl or substituted phenyl, where said substituted phenyl may be substituted with 1 to 3 of $C_1$ to $C_4$ alkyl, halogen, hydroxy, cyano, carboxamido, nitro, or $C_1$ to $C_4$ alkoxy, and the pharmaceutically acceptable salts thereof. These compounds are useful in treating migraine and other disorders and are new. These compounds are useful psychotherapeutics and are potent serotonin (5-HT$_1$) agonists and may be used in the treatment of depression, anxiety, eating disorders, obesity, drug abuse, cluster headache, migraine, pain, and chronic paroxysmal hermicrania and headache associated with vascular disorders, and other disorders arising from deficient serotonergic neurotransmission. The compounds can also be used as centrally acting antihypertensives and vasodilators.

6 Claims, No Drawings

FOREIGN PATENT DOCUMENTS

| | | |
|---|---|---|
| 9321178 | 10/1993 | WIPO . |
| 9321180 | 10/1993 | WIPO . |
| 9323396 | 11/1993 | WIPO . |
| 9424127 | 10/1994 | WIPO . |
| 9425023 | 11/1994 | WIPO . |
| 9506636 | 3/1995 | WIPO . |

5-ARYLINDOLE DERIVATIVES

This is the national stage application filed under 35 U.S.C. 371 of PCT/IB94/00195 filed Jul. 4, 1994 which is a CIP of 08/115,282 filed Aug. 31, 1992 now abandoned.

BACKGROUND OF THE INVENTION

The present invention relates to indole derivatives, to processes and intermediates for their preparation, to pharmaceutical compositions containing them and to their medicinal use. The active compounds of the present invention are useful in treating migraine and other disorders.

U.S. Pat. Nos. 4,839,377 and 4,855,314 and European Patent Application Publication Number 313397 refer to 5-substituted 3-aminoalkyl indoles. The compounds are said to be useful for the treatment of migraine.

British Patent Application 040279 refers to 3-aminoalkyl-1 H-indole-5-thioamides and carboxamides. The compounds are said to be useful in treating hypertension, Raymond's disease and migraine.

European Patent Application Publication Number 303506 refers to 3-poly:hydro-pyridyl-5-substituted-1 H-indoles. The compounds are said to have 5-HT$_1$ receptor agonist and vasoconstrictor activity and to be useful in treating migraine.

European Patent Application Publication Number 354777 refers to N-piperidinyl:indolyl:ethyl-alkane sulfonamide derivatives. The compounds are said to have 5-HT$_1$ receptor agonist and vasoconstrictor activity and to be useful in treating cephalic pain.

European Patent Application Publication Numbers 438230, 494774, and 497512 refers to indole-substituted five-membered heteroaromatic compounds. The compounds are said to have 5-HT$_1$-like receptor agonist activity and to be useful in the treatment of migraine and other disorders for which a selective agonist of these receptors is indicated.

European Patent Application Publication Number 313397 refers to 5-heterocyclic indole derivatives. The compounds are said to have exceptional properties for the treatment and prophylaxis of migraine, cluster headache, and headache associated with vascular disorders. These compound are also said to have exceptional "5HT$_1$-like" receptor agonism.

International Patent Application PCT/GB91/00908 and International Patent Application WO 91/18897 refers to 5-heterocyclic indole derivatives. The compounds are said to have exceptional properties for the treatment and prophylaxis of migraine, cluster headache, and headache associated with vascular disorders. These compound are also said to have exceptional "5-HT$_1$-like" receptor agonism.

European Patent Application Publication Number 457701 refers to aryloxy amine derivatives as having high affinity for 5-HT$_{1D}$ serotonin receptors. These compounds are said to be useful for treating diseases related to serotonin receptor dysfunction, for example, migraine.

European Patent Application Publication Number 497512 A2 refers to a class of imidazole, triazole, and tetrazole derivatives which are selective agonists for 5-HT$_1$-like receptors. These compounds are said to be useful for treating migraine and associated disorders.

International patent application WO 9300086 describes a series of tetrahydrocarbazone derivatives as 5-HT$_1$ receptor agonists useful for the treatment of migraine and related conditions.

Y. Yang, et. al describe the synthesis of 5-arylindoles in *Heterocycles*, Vol. 34, 1395 (1992) via palladium catalyzed cross-coupling reactions.

SUMMARY OF THE INVENTION

The present invention relates to compounds of the formula

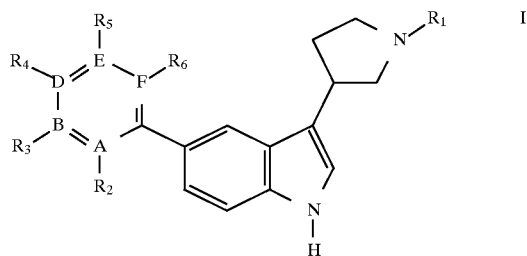

wherein A, B, D, E, and F are each independently nitrogen or carbon; $R_1$ is hydrogen, $C_1$ to $C_6$ alkyl, —(CH$_2$)$_n$R$_7$, or $C_1$ to $C_3$ alkyl-aryl; $R_2$, $R_3$, $R_4$, $R_5$ and $R_6$ are each independently hydrogen, $C_1$ to $C_6$ alkyl, aryl, $C_1$ to $C_3$ alkyl-aryl, halogen (e.g. fluorine, chlorine, bromine or iodine), cyano, nitro, —(CH$_2$)$_m$NR$_8$R$_9$, —(CH$_2$)$_m$OR$_9$, —SR$_9$, —SO$_2$NR$_8$R$_9$, —(CH$_2$)$_m$NR$_8$SO$_2$R$_9$, —(CH$_2$)$_m$NR$_8$CO$_2$R$_9$, —(CH$_2$)$_m$NR$_8$COR$_9$, —(CH$_2$)$_m$CONR$_7$R$_9$, or —(CH$_2$)$_m$CO$_2$R$_9$; $R_2$ and $R_3$, $R_3$ and $R_4$, $R_4$ and $R_5$, and $R_5$ and $R_6$ may be taken together to form a five- to seven-membered alkyl ring, a six-membered aryl ring, a five- to seven-membered heteroalkyl ring, having 1 heteroatom of N, O, or S, or a five- to six- membered heteroaryl ring having 1 or 2 heteroatoms of N, O, or S; $R_7$ is OR$_{10}$, —SR$_{10}$, —SO$_2$NR$_{10}$R$_{11}$, —NR$_{10}$SO$_2$R$_{11}$, —NR$_{10}$CO$_2$R$_{11}$, —NR$_{10}$COR$_{11}$, —CONR$_{10}$R$_{11}$, or —CO$_2$R$_{10}$; R$_8$, R$_9$, R$_{10}$ and R$_{11}$ are independently hydrogen, $C_1$ to $C_6$ alkyl, or $C_1$ to $C_3$ alkyl-aryl; m is 0, 1, or 2; n is 2, 3, or 4; and the above aryl groups and the aryl moieties of the above alkyl-aryl groups are each independently phenyl or substituted phenyl, wherein said substituted phenyl may be substituted with one to three of $C_1$ to $C_4$ alkyl, halogen (e.g. fluorine, chlorine bromine or iodine), hydroxy, cyano, carboxamido, nitro, or $C_1$ to $C_4$ alkoxy, and the pharmaceutically acceptable salts thereof. These compounds are potent 5-HT$_1$, agonists with selectivity for the 5-HT$_{1D}$ receptor and are useful in treating migraine and other disorders.

The compounds of the invention include all optical isomers of formula I (e.g. R and S stereogenicity at any chiral site) and their racemic, diastereomeric, or epimeric mixtures.

Unless otherwise indicated, the alkyl and alkenyl groups referred to herein, as well as the alkyl moieties of other groups referred to herein (e.g. alkoxy), may be linear or branched, and they may also be cyclic (e.g. cyclopropyl, cyclobutyl, cyclopentyl, or cyclohexyl) or be linear or branched and contain cyclic moieties.

Preferred compounds of the invention are compounds of the formula I wherein B or E is nitrogen; A or F is carbon; $R_1$ is hydrogen, $C_1$ to $C_3$ alkyl, or —(CH$_2$)$_2$OCH$_3$.

The following compounds are particularly preferred:
3-(N-methylpyrrolidin-3-yl)-5-(pyrimid-5-yl)-1 H-indole;

5-(pyrimid-5-yl)-3-(pyrrolidin-3-yl)-1 H-indole;

3-[N-(2-methoxyethyl)pyrrolidin-3-yl]-5-(pyrimid-5-yl)-1 H-indole;

3-(N-ethylpyrrolidin-3-yl)-5-(pyrimid-5-yl)-1 H-indole;

5(3-cyanopyrid-5-yl)-3-(N-methylpyrrolidin-3-yl)-1 H-indole;

5(3-cyanopyrid-5-yl)-3-(pyrrolidin-3-yl)-1 H-indole;

5-(3-cyanopyrid-5-yl)-1-H-3-[N-(2methoxyethyl) pyrrolidin-3-yl]-indole; and 3-(N-methylpyrrolidin-3-yl)-5-(1,2,4-triazin-3-yl)-1 H-indole.

The present invention also relates to a compound of the formula

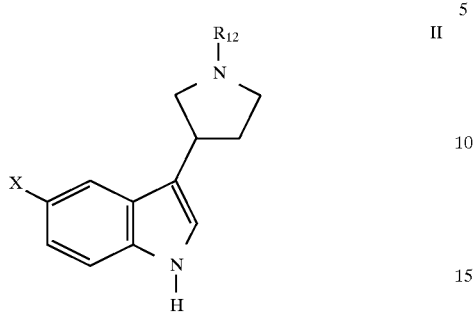

II wherein X is halogen [chloride, bromide, iodide] or —OSO$_2$CF$_3$ and R$_{12}$ is hydrogen, methyl, or benzyl. These compounds are useful as intermediates in preparing compounds of formula I The present invention also relates to a pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound of the formula I or a pharmaceutically acceptable salt thereof effective in treating such condition and a pharmaceutically acceptable carrier.

The present invention also relates to a method for treating a condition selected from hypertension, depression, anxiety, eating disorders, obesity, drug abuse, cluster headache, migraine, pain and chronic paroxysmal hemicrania and headache associated with vascular disorders comprising administering to a mammal (e.g., a human) requiring such treatment an amount of a compound of the formula I or a pharmaceutically acceptable salt thereof effective in treating such condition.

The present invention also relates to a method for treating disorders arising from deficient serotonergic neurotransmission (e.g., depression, anxiety, eating disorders, obesity, drug abuse, cluster headache, migraine, pain and chronic paroxysmal hemicrania and headache associated with vascular disorders) comprising administering to a mammal (e.g., a human) requiring such treatment an amount of a compound of the formula I or a pharmaceutically acceptable salt thereof effective in treating such condition.

The present invention also relates to a method for treating disorders arising from deficient serotonergic neurotransmission (e.g., depression, anxiety, eating disorders, obesity, drug abuse, cluster headache, migraine, pain and chronic paroxysmal hemicrania and headache associated with vascular disorders) comprising administering to a mammal (e.g., a human) requiring such treatment an amount of a compound of the formula I or a pharmaceutically acceptable salt thereof effective in treating such condition.

DETAILED DESCRIPTION OF THE INVENTION

The compounds of formula I can be prepared via the following reaction scheme:

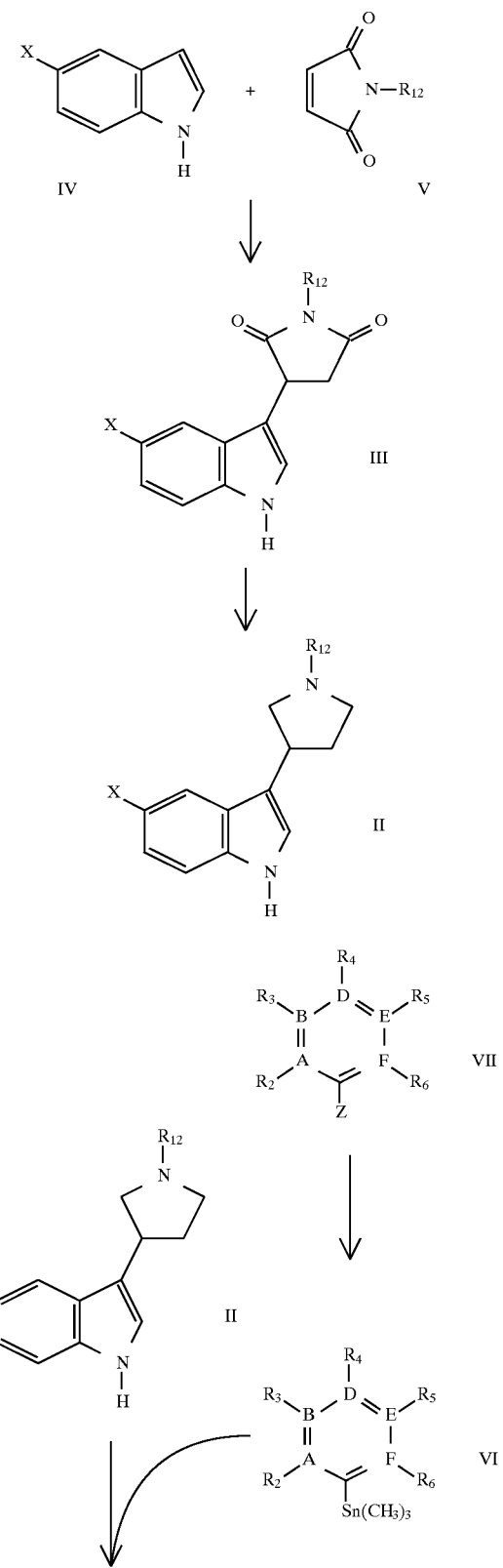

-continued

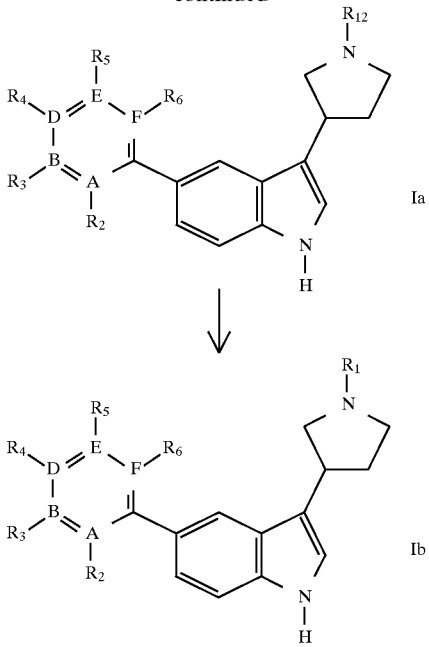

Compounds of formula III wherein X is halogen [chloride, bromide, iodide] or —OSO$_2$CF$_3$ and R$_{12}$ is hydrogen, methyl, or benzyl can be prepared from the condensation of a compound of formula IV wherein X is as defined above with a compound of formula V wherein R$_{12}$ is as defined above in an inert solvent. Suitable inert solvents include C$_1$ to C$_3$ alcohols, acetic acid, formic acid, and N,N-dimethylformamide. The preferred solvent is acetic acid. The reaction is usually conducted at a temperature of from about 65° C. to about 154° C., preferably about 100°C. to about 110°C.

Compounds of formula 11 wherein X and R$_{12}$ are as defined above can be prepared via the reduction of a compound of formula III wherein R$_{12}$ is as defined above in an inert solvent. Suitable reducing agents include lithium aluminum hydride, lithium borohydride, and diborane. Uthium aluminum hydride is the preferred reducing agent. Suitable inert solvents include tetrahydrofuran, dioxane, diethyl ether, and other ethers. Tetrahydrofuran is the preferred solvent. The reaction is usually conducted at a temperature of from about 25° C. to about 100°C., preferably at about 65° C.

Compounds of formula VI wherein A, B, D, E, F. R$_2$, R$_3$, R$_4$, R$_5$, and R$_6$ are as defined above can be prepared from a compound of formula VII wherein A, B, D, E, F, R$_2$, R$_3$, R$_4$, R$_5$, and R$_6$ are as defined above, and Z is halogen [chloride, bromide, iodide] or —OSO$_2$CF$_3$ via a transition metal catalyzed insertion reaction using hexamethyiditin in an inert solvent, usually in the presence of a base, lithium chloride, and butylated hydroxytoluene [i.e., 2,6-di-tert-butyl-4 -methylphenol, BHT]. Suitable catalysts are of palladium (II) and palladium (0) species, such as palladium (II) acetate, palladium (II) chloride, bis(triphenylphosphine) palladium (II) chloride, and tetrakis(triphenylphoshine) palladium(0). The preferred catalyst is tetrakis (triphenylphoshine)palladium(0). Suitable inert solvents include ethers, such as tetrahydrofuran and dioxane, acetonitrile, N,N-dimethylformamide, and N-methylpyrrolidin-2-one. Dioxane is the preferred inert solvent. Suitable bases include tertiary amines, sodium bicarbonate, and sodium carbonate. The preferred base is triethylamine. The reaction is usually conducted at a temperature between about 70° C. and about 210° C., preferably between about 90° C. and 154° C.

Compounds of formula Ia wherein A, B, D, E, F, R$_2$, R$_3$, R$_4$, R$_5$, R$_6$, and R$_{12}$ are as defined above can be prepared by the transition metal catalyzed aryl cross-coupling reaction between a compound of formula 11 wherein X and R$_{12}$ are as defined above and a compound of formula VI wherein A, B, D, E, F, R$_2$, R$_3$, R$_4$, R$_5$, and R$_6$ are as defined above in an inert solvent, usually in the presence of a base, lithium chloride, and butylated hydroxytoluene [i.e., 2,6di-tert-butyl-4 -methylphenol, BHT]. Suitable catalysts are palladium (II) and palladium (0) species, such as palladium (II) acetate, palladium (II) chloride, bis(triphenylphosphine) palladium (II) chloride, tetrakis(triphenylphoshine) palladium(0). The preferred catalyst is bis (triphenylphosphine)palladium (II) chloride. Suitable inert solvents include acetonitrile, N,N-dimethylformamide, and N-methylpyrrolidin-2-one. N,N-dimethylformamide is the preferred inert solvent. Suitable bases include tertiary amines, sodium bicarbonate, and sodium carbonate. The preferred base is triethylamine. The reaction is usually conducted at a temperature between about 70° C. and about 210°C., preferably between about 90° C and 154° C.

Compounds of formula Ib wherein A, B, D, E, F, R$_1$, R$_2$, R$_3$, R$_4$, R$_5$, and R$_6$ are as defined above can be prepared from a compound of formula Ia wherein R$_{12}$ is benzyl, and A, B, D, E, F, R$_2$, R$_3$, R$_4$, R$_5$, and R$_6$ are as defined above via a reductive amination using an aldehyde of the formula R$_{13}$CHO, where R$_{13}$ is C$_1$ to C$_5$ alkyl, —(CH$_2$)$_8$R$_7$, or C$_1$ to C$_2$ alkyl-aryl, s is 1, 2, or 3, and R$_7$ is as defined above, along with a transition metal catalyst, and a hydrogen source in an inert solvent. Suitable catalysts include palladium on carbon, Raney nickel, platinum oxide, and palladium hydroxide on carbon. The preferred catalyst is palladium hydroxide on carbon. Suitable hydrogen sources include hydrogen gas, ammonium formate, and formic acid. Hydrogen gas at a pressure of from about one to about three atmospheres is the preferred hydrogen source. Three atmospheres of hydrogen gas is the preferred pressure. Suitable solvents include C$_1$ to C$_4$ alcohols, acetonitrile, N,N-dimethylformamide, and N-methylpyrrolidine. Ethanol is the preferred solvent. The reaction is usually conducted at a temperature of from about 25° C. to about 100° C., preferably about 25° C. to about 50° C.

Compounds of formula IV, formula V, and formula VII are either commercially available or can be prepared using methods known to one skilled in the art. Aldehydes of the formula R$_{13}$CHO wherein R$_{13}$ is as defined above are also either commercially available or can be prepared using methods known to one skilled in the art.

Unless indicated otherwise, the pressure of each of the above reactions is not critical. Generally, the reactions will be conducted at a pressure of from about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where $R_2$ contains a carboxylate, are capable of forming base salts with various pharmacologically acceptable cations. Examples of such salts include the alkali metal or alkaline-arth metal salts and particular, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction of maximum product of yields of the desired final product.

The compounds of the formula I and the pharmaceutically acceptable salts thereof (hereinafter, also referred to as the active compounds of the invention) are useful psychotherapeutics and are potent serotonin (5-HT$_1$) agonists with selectivity for the 5-HT$_{1D}$receptor and may be used in the treatment of depression, anxiety, eating disorders, obesity, drug abuse, cluster headache, migraine, chronic paroxysmal hemicrania and headache associated with vascular disorders, pain, and other disorders arising from deficient serotonergic neurotransmission. The compounds can also be used as centrally acting antihypertensives and vasodilators. The active compounds of the invention can be evaluated as anti-migraine agents by testing the extent to which they mimic sumatriptan in contracting the dog isolated saphenous vein strip [P.P.A. Humphrey et al., Br. J. Pharmacol., 94, 1128 (1988)]. This effect can be blocked by methiothepin, a known serotonin antagonist. Sumatriptan is known to be useful in the treatment of migraine and produces a selective increase in carotid vascular resistance in the anesthetized dog. It has been suggested [W. Fenwick et al., Br. J. Pharmacol., 96, 83 (1989)] that this is the basis of its efficacy.

The active compounds of the present invention can also be evaluated via the plasma protein extravasation response within the dura mater of guinea pigs following unilateral electrical trigeminal ganglion stimulation, as described in Markowitz et al., J. Neurosci., 7 (12), 41294136 (1987). The extent to which they mimic sumatriptan, in terms of both potency and efficacy, is determined in this assay.

The serotonin 5HT$_1$ agonist activity is measured in in vitro receptor binding assays as described for the 5-HT$_{1A}$ receptor using rat cortex as the receptor source and [$^3$H]-8-OH-DPAT as the radioligand [D. Hoyer et al. Eur. J. Pharm., Vol. 118, 13 (1985)] and as described for the 5-HT$_{1D}$ receptor using bovine caudate as the receptor source and [$^3$H] serotonin as the radioligand [R. E. Heuring and S. J. Peroutka, J. Neuroscience, Vol.7, 894 (1987)]. 5-HT agonist activity is defined by agents with affinities (IC$_{50}$S) of 250 nM or less at either binding assay.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Uquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., migraine) is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 $\mu$g to 1000 $\mu$g of the compound of the invention. The overall daily dose with an aerosol will be within the range 100 $\mu$g to 10 mg. Administration may be several times daily, for example 2, 3, 4 or 8 times, giving for example, 1, 2 or 3 doses each time.

The following Examples illustrate the preparation of the compounds of the present invention and are not intended to limit in any way the scope of the claims. Commercial reagents were utilized without further purification. Melting points are uncorrected. NMR data are reported in parts per million (d) and are referenced to the deuterium lock signal from the sample solvent. Specific rotations were measured at room temperature using the sodium D line (589 nm). Unless otherwise stated, all mass spectrum were performed using electron impact (El, 70 eV) conditions. Chromatography refers to column chromatography performed using 32–63 $\mu$m silica gel and executed under nitrogen pressure (flash chromatography) conditions. Room temperature refers to 20°–25° C.

EXAMPLE 1

3-(N-Methylpyrrolidin-3-yl)-5-(pyrimid-5-yl)-1H-indole

A mixture of 5-bromo-3-(N-methylpyrrolidin-3-yl)-1 H-indole (0.450 g, 1.86 mmol), 5-trimethylstannylpyrimidine (0.518 g, 1.86 mmol), bis(triphenylphosphine)palladium(II) chloride (0.100 g), triethylamine (0.84 mL, 6.03 mmol, 3.2 eq), lithium chloride (0.254 g), and 2,6-di-tert-butyl-4-methylphenol (3.0 g) in anhydrous N,N-dimethylformamide (8 mL) was heated at reflux under nitrogen for 4 hours. The resulting reaction mixture was evaporated under reduced pressure, and the residue was column chromatographed using silica gel (approximately 25 g) and elution with 9:1:0.1 [methylene chloride/methanol/ammonium hydroxide] afforded the title compound (0.089 g, 0.32 mmol, 17%) as an off-white solid: mp, 140.0°–143.0° C.; TLC R$_f$=0.20 in 9:1:0.1 [methylone chloride/methanol/ammonium hydroxide]; $^1$H NMR (CD$_3$OD) $\delta$ 9.05 (s, 2 H), 9.03 (s, 1 H), 7.87 (d, J=1.1 Hz, 1 H), 7.47 (d, J=8.4 Hz, 1 H), 7.39 (dd, J=1.6 and 8.5 Hz, 1 H), 7.16 (s, 1 H), 4.90 (s, 1 exchangeable H), 3.78-3.66 (m, 1 H), 3.16 (t, J=8.7 Hz, 1 H), 2.92-2.84 (m, 1 H), 2.72-2.59 (m, 2 H), 2.42 (s, 3 H), 2.42-2.33 (m, 1 H), 2.10-1.99 (m, 1 H); $^{13}$C NMR (CD$_3$OD) d 156.6, 155.9, 138.9, 137.7, 129.0, 125.4,123.2, 121.4, 119.7, 118.7, 113.6, 63.5, 57.1, 42.6, 36.3, 33.2; FAB LRMS (m/z, relative intensity) 279 ([MH]$^+$, 100); HRMS calculated for C$_{17}$ H$_{18}$ N$_4$ 278.1533, found 278.1520.

EXAMPLE 2

5-(5-Cyanopyrid-3-yl)-3-(N-methylpyrrolidin-3-yl)-1 H-indole

A mixture of 5-bromo-3-(N-methylpyrrolidin-3-yl)-1 H-indole (0.500 g, 1.79 mmol), 5-cyano-3-trimethylstannylpyridine (0.525 g, 1.97 mmol, 1.1 eq), bis(triphenylphosphine)palladium(II) chloride (0.628 g, 0.90 mmol, 0.5 eq), triethylamine (1.19 mL, 8.59 mmol, 4.8 eq), lithium chloride (0.235 g, 5.55 mmol, 3.1 eq), and 2,6-di-tert-butyl-4-methylphenol (40 mg) in anhydrous acetonitrile (5 mL) was heated at reflux under nitrogen for 20 hours. The resulting reaction mixture was evaporated under reduced pressure, and the residue was column chromatographed using silica gel (approx 50 g) and elution with 9:1:0.1 [methylene chloride/methanol/ammonium hydroxide] to afford the title compound (0.060 g, 0.20 mmol, 11%) as a clear, pale brown oil: LRMS (m/z, relative intensity) 302 (M+, 29), 245 (8), 57 (100); HRMS calculated for C$_{19}$ H$_{18}$ N$_4$ 302.1528, found 302.1533.

EXAMPLE 3

5-Bromo-3-(N-methylpyrrolidin-3-yl)-1 H-indole

To a stirred mixture of lithium aluminum hydride (1.10 g, 29.0 mmol, 2.2 eq) in anhydrous tetrahydrofuran (60 mL) at 0° C. was added 3-(5-bromoindol-3-yl)-N-methylsuccinimide (4.00 g, 13.02 mmol) portionwise cautiously. The resulting reaction mixture was heated at reflux under nitrogen for 2 hours. The reaction mixture was then cooled, and sodium sulfate decahydrate (approximately 20 g) was added slowly and cautiously, followed by the addition of water (approximately 2 mL) and ethyl acetate (200 mL). The resulting mixture was stirred at room temperature under nitrogen for 2 hours, and then filtered through Celite®. The filtrate was evaporated under reduced pressure to afford the title compound (2.64 g, 9.46 mmol, 73%) as an off-white solid: mp, 163.0°–164.0° C.; TLC R$_f$ =0.30 in 9:1:0.1 [methylene chloride/methanol/ammonium hydroxide]; $^1$ H NMR (DMSO-d$_6$) $\delta$ 11.0 (br m, NH), 7.74 (d, J=1.3 Hz, 1 H), 7.29 (d, J=8.8 Hz, 1 H), 7.20 (br s, 1 H), 7.15 (dd, J=1.7 and 8.6 Hz, 1 H), 3.55-3.45 (m, 1 H), 2.88 (t, J=8.2 Hz, 1 H), 2.62-2.42 (m, 3 H), 2.29 (s, 3 H), 2.28-2.21 (m, 1 H), 1.90-1.80 (m, 1 H); $^{13}$C NMR (DMSO-d$_6$) d 135.4,128.2,123.4, 122.9,121.1, 118.3, 113.5,110.8, 62.6, 56.0, 42.1, 34.4, 32.2; HMRS calculated for C$_{13}$H$_{15}$BrN$_2$ 278.0415, found 278.0355.

EXAMPLE 4

3-(5-Bromoindol-3-yl)-N-methylsuccinimide

A solution of 5-bromoindole (4.00 g, 20.40 mmol) and N-methylmaleimide (5.00 g, 45.00 mmol, 2.2 eq) in glacial acetic acid (50 mL) was heated at reflux under nitrogen for 120 hours. The resulting reaction mixture was evaporated under reduced pressure, and the residue was stirred vigorously in a solution of ether/methylene chloride (9:1, 200 mL) for 2 hours. Undissolved solid was filtered to afford the title compound (4.34 g, 14.13 mmol, 69%) as a pale yellow solid: mp, 196.0°–197.0° C.; TLC R$_f$=0.3 in diethyl ether; $^1$H NMR (CDCl$_3$) $\delta$ 8.35 (br m, NH), 7.56 (d, J=1.5 Hz, 1

H), 7.29 (dd, J=1.7 and 8.6 Hz, 1 HO, 7.22 (d, J=8.7 Hz, 1 H), 7.08 (br s, 1 H), 4.26 (dd, J=5.1 and 9.4 Hz, 1 H), 3.28 (dd, J=9.4 and 18.3 Hz, 1 H), 3.11 (s, 3 H), 2.87 (dd, J=5.1 and 18.3 Hz, 1 H); FAB LRMS (m/z, relative intensity, $NH_4+$ as ionization source) 326 ([M(with $^{81}$Br)-$NH_4$]$^+$, 100), 324 ([M(with $^{79}$Br)-$NH_4$]$^+$, 96), 309 ([M(with $^{81}$Br)-H]$^+$, 21), 307 ([M(with $^{79}$Br)-H]$^+$, 20). Anal. calcd for $C_{13}H_{11}BrN_2O_2$: C, 50.84; H, 3.61; N, 9.12. Found: C, 50.67; H, 3.43; N, 9.00.

EXAMPLE 5

5-Trimethylstannylpyrimidine

A mixture of 5-bromopyrimidine (4.00 g, 25.16 mmol), hexamethylditin (9.06 g, 27.67 mmol, 1.1 eq), lithium chloride (1.27 g, 30.19 mmol, 1.2 eq) tetrakis(triphenylphosphine) palladium(0) (1.13 g, 0.98 mmol, 0.04 eq), and 2,6-di-tert-butyl-4 -methylphenol (0.08 g) in anhydrous 1,4dioxane (45 mL) has heated at reflux under nitrogen for 16 hours. The resultant reaction mixture was evaporated under reduced pressure, and the residue was directly column chromatographed using silica gel (approximately 250 g) and elution with ethyl acetate/hexanes (1:1) to afford the title compound (4.75 g, 19.6 mmol, 78%) as a clear, pale yellow liquid: TLC $R_f$=0.6 in 1:1 ethyl acetate/hexanes; $^1$H NMR ($CDCl_3$) δ 9.11 (s, 1 H), 8.70 (s, 2 H), 0.38 (s, 9 H).

EXAMPLE 6

5-Cyano-3-trimethylstannylpyridine

A mixture of 3-bromo-5-cyanopyridine (0.58 g, 3.17 mmol) [C. Zwart and J. P. Wibaut, *Rec. trav. chim.*, 74, 1062 (1955)], lithium chloride (0.161 g, 3.80 mmol, 1.2 eq), 2,6di-tert-butyl-4-methylphenol (12 mg),tetrakis (triphenylphosphine)palladium(0) (0.145 g, 0.13 mmol, 0.04 eq), and hexamethyiditin (1.14 g, 3.49 mmol, 1.1 eq) in anhydrous dioxane (6 mL) was heated at reflux under nitrogen for 4.5 hours. The resulting reaction mixture was evaporated under reduced pressure, and the residue was column chromatographed using silica gel (approx 50 g) and elution with 3:1 [hexanes/ether] to afford the title compound (0.68 g, 2.55 mmol, 80%) as a white solid: mp, 77.0°–79.0° C.; IR (KBr) 2231 cm$^{-1}$; $R_f$=0.4 in diethyl ether; $^1$H NMR ($CDCl_3$) δ 8.79-8.77 (m, 2 H), 8.01 (dd, J=2.1 and 1.5 Hz, 1 H), 0.38 (s, 9 H); $^{13}$C NMR ($CDCl_3$) δ 158.4, 151.7,146.4, 138.3, 117.1, 110.3, 3.0.

I claim:

1. A compound of the formula

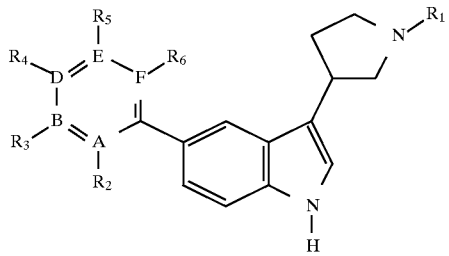

wherein A, B, D, E, and F are each independently nitrogen or carbon, further wherein only two of A, B, D, E, and F are nitrogen; $R_1$ is hydrogen, $C_1$ to $C_6$ alkyl, —$(CH_2)_nR_7$, or $C_1$ to $C_3$ alkyl-aryl; $R_2$, $R_3$, $R_4$, $R_5$ and $R_6$ are each independently hydrogen, $C_1$ to $C_6$ alkyl, aryl, $C_1$ to $C_3$ alkyl-aryl, halogen, cyano, nitro, —$(CH_2)_mNR_8R_9$, —$(CH_2)_mOR_9$, —$SR_9$, —$SO_2NR_8R_9$, —$(CH_2)_mNR_8SO_2R_9$, —$(CH_2)_mNR_8CO_2R_9$, —$(CH_2)_mNR_8COR_9$, —$(CH_2)_mCONR_7R_9$, or —$(CH_2)_mCO_2R_9$; $R_2$ and $R_3$, $R_3$ and $R_4$, $R_4$ and $R_5$, and $R_5$ and $R_6$ may be taken together to form a five- to seven-membered alkyl ring, a six-membered aryl ring, a five- to seven-membered heteroalkyl ring, having 1 heteroatom of N, O, or S, or a five- to six-membered heteroaryl ring having 1 or 2 heteroatoms of N, O, or S; $R_7$ is —$OR_{10}$, —$SR_{10}$, —$SO_2NR_{10}$ $_{R11}$, —$NR_{10}SO_2R_{11}$, —$NR_{10}CO_2R_{11}$, —$NR_{10}COR_{11}$, —$CONR_{10}R_{11}$, or —$CO_2R_{10}$; $R_8$, $R_9$, $R_{10}$, and $R_{11}$ are each independently hydrogen, $C_1$ to $C_6$ alkyl, or $C_1$ to $C_3$ alkyl-aryl; m is 0, 1, or 2; n is 2, 3, or 4; and the above aryl groups and the aryl moieties of the above alkyl-aryl groups are each independently phenyl or substituted phenyl, wherein said substituted phenyl may be substituted with one to three of $C_1$ to $C_4$ alkyl, halogen, hydroxy, cyano, carboxamido, nitro, or $C_1$ to $C_4$ alkoxy, with the proviso that when $R_1$ is hydrogen or $C_1$ to $C_6$ alkyl then $R_2$ and $R_3$, $R_3$ and $R_4$, $R_4$ and $R_5$, and $R_5$ and $R_6$ must be taken together to form a five- to seven-membered alkyl ring, a six-membered aryl ring, a five- to seven-membered heteroalkyl ring, having 1 heteroatom of N, O, or S, or a five- to six-membered heteroaryl ring having 1 or 2 heteroatoms of N, O, or S, and the pharmaceutically acceptable salts thereof.

2. A compound according to claim 1 wherein B or E is nitrogen; A or F is carbon; $R_1$ is hydrogen, $C_1$ to $C_3$ alkyl, or —$(CH_2)_2OCH_3$.

3. A pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound according to claim 1 effective in treating such condition and a pharmaceutically acceptable carrier.

4. A pharmaceutical composition for treating disorders arising from deficient serotonergic neurotransmission comprising an amount of a compound according to claim 1 effective in treating such a disorder and a pharmaceutically acceptable carrier.

5. A method for treating a condition selected from hypertension, depression, anxiety, eating disorders, obesity, drug abuse, cluster headache, migraine, pain, and chronic paroxysmal hemicrania and headache associated with vascular disorders comprising administering to a mammal requiring such treatment an amount of a compound according to claim 1 effective in treating such condition.

6. A method for treating disorders arising from deficient serotonergic neurotransmission comprising administering to a mammal requiring such treatment an amount of a compound according to claim 1 effective in treating such condition.

* * * * *